United States Patent [19]

Madrange et al.

[11] Patent Number: 4,820,308
[45] Date of Patent: Apr. 11, 1989

[54] DETERGENT COSMETIC COMPOSITIONS CONTAINING A SOAP AND CATIONIC COMPOUND AND DIRECT DYE

[75] Inventors: Annie Madrange, Saint Germain en Laye; Patrick Canivet, Paris, both of France

[73] Assignee: L'OREAL, Paris, France

[21] Appl. No.: 111,498

[22] Filed: Oct. 16, 1987

Related U.S. Application Data

[62] Division of Ser. No. 786,247, Oct. 10, 1985, Pat. No. 4,710,314.

[30] Foreign Application Priority Data

Oct. 12, 1984 [FR] France ..................... 85 589

[51] Int. Cl.⁴ .................. A61K 7/13; C11D 3/40; C11D 3/37
[52] U.S. Cl. ........................... 8/405; 8/527; 132/202; 252/117; 252/132; 252/174.23; 252/174.15; 252/544; 252/547; 252/DIG. 2; 252/DIG. 13; 424/70
[58] Field of Search ........... 252/108, 117, 132, 174.23, 252/174.15, 544, 547, DIG. 2, DIG. 13; 424/47, 70, 78; 8/405, 527

[56] References Cited

U.S. PATENT DOCUMENTS

| | | | |
|---|---|---|---|
| 3,964,500 | 6/1976 | Drakoff | 132/7 |
| 3,996,146 | 12/1976 | Tarasov et al. | 252/142 |
| 4,048,301 | 9/1977 | Papantoniou | 424/70 |
| 4,080,310 | 3/1978 | Guttler | 252/544 |
| 4,185,087 | 1/1980 | Morlino | 424/70 |
| 4,220,548 | 9/1980 | Hashimoto | 252/106 |
| 4,477,375 | 10/1984 | Grollier | 252/542 |
| 4,532,127 | 7/1985 | Feinland et al. | 424/62 |
| 4,597,962 | 7/1986 | Grollier et al. | 424/47 |
| 4,673,568 | 6/1987 | Grollier et al. | 424/47 |

FOREIGN PATENT DOCUMENTS

| | | |
|---|---|---|
| 0017121 | 10/1980 | European Pat. Off. . |
| 2548019 | 1/1985 | France . |
| 167699 | 10/1983 | Japan . |
| 2058103 | 4/1981 | United Kingdom . |
| 2143434 | 2/1985 | United Kingdom . |

Primary Examiner—Prince E. Willis
Attorney, Agent, or Firm—Fleit, Jacobson, Cohn & Price

[57] ABSTRACT

Detergent cosmetic composition stable on storage, comprising in a cosmetically acceptable aqueous medium:
(a) a soap,
(b) a silicone cationic polymer consisting of a polysiloxane in which one or more of the silicon atoms are substituted with an aliphatic amino group,
(c) a cationic surfactant, and
(d) a cationic polymer chosen from cationic polysaccharides and cationic cyclopolymers
(e) a direct dye.

16 Claims, No Drawings

DETERGENT COSMETIC COMPOSITIONS CONTAINING A SOAP AND CATIONIC COMPOUND AND DIRECT DYE

This is a divisional of application Ser. No. 786,247, filed Oct. 10, 1985, now U.S. Pat. No. 4,710,314.

The present invention relates to new stable detergent cosmetic compositions containing a soap and cationic compounds.

It is well known to use, in detergent cosmetic compositions such as shampoos, cationic surfactants or cationic polymers. These cationic surfactants generally contribute to imparting properties of disentangling, softness and sheen to the hair, but they tend to make the hair lank.

Cationic polymers also possess advantageous properties and contribute generally to improving the disentangling properties. In certain cases, however, the use of such polymers gives the hair excessive texture and body, thereby producing a coating and making the hair hardened or slimy.

Furthermore, anionic surfactants, and the use thereof in detergent cosmetic compositions such as shampoos, are known.

In multi-stage washing processes, use has also been made of shampoos containing an anionic surfactant, followed by a rinsing composition or "rinse" containing one or more cationic compounds.

It has, however, been found that it was not possible to combine anionic surfactants with cationic compounds without problems being encountered, since a combination of this kind generally gave rise to products which were insoluble in water or unstable as a result of the incompatibility of the anionic surfactants with the cationic compounds.

The Applicant Company has discovered that it was possible to prepare a single, stable, detergent and treating composition which did not possess the abovementioned disadvantages by combining, in one and the same composition, a particular anionic surfactant chosen from soaps and a combination of cationic compounds.

The subject of the invention is hence detergent cosmetic compositions which are stable on storage and contain, in an aqueous medium, a soap and cationic compounds.

The subject of the invention is also a washing process employing such compositions.

Further subjects of the invention will emerge on reading the description and examples which follow.

The detergent cosmetic composition, stable on storage, according to the invention, is essentially characterised in that it comprises, in a cosmetically acceptable aqueous medium, a soap, a silicone cationic polymer, a cationic surfactant and a cationic polymer chosen from cationic polysaccharides and cationic cyclopolymers.

The soaps used according to the invention are chosen from alkali metal salts, alkanolamine salts (such as monoethanolamine, diethanolamine, triethanolamine, 2-amino-2-methyl-1-propanol, 2-amino-2-methyl-1,3-propanediol and triisopropanolamine salts) of $C_{12}$-$C_{18}$ fatty acids in which the fatty chain is saturated or unsaturated. Among fatty acids, lauric, palmitic or oleic acids may be mentioned more especially.

The soaps which are especially preferred are the triethanolamine or 2-amino-2-methyl-1-propanol salts of lauric, palmitic or oleic acid.

The silicone cationic polymers used according to the invention are polysiloxanes in which one or more of the silicon atoms in the chain bear(s) an aliphatic amino group in which the amine group is primary, secondary, tertiary or quaternary. The expression "aliphatic amino" encompasses amino alkyl or amino(hydroxyalkyl) radicals in which the alkyl chain may be interrupted by nitrogen or oxygen atoms.

Silicone cationic polymers are described, in particular, in the CFTA dictionary (3rd edition 1982, published by The Cosmetic, Toiletry and Fragrance Association, Inc.).

Among preferred silicone cationic polymers, there may be mentioned the polymer corresponding to the formula:

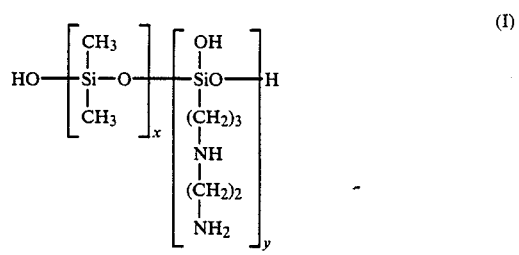

(I)

in which x and y are integers which depend on the molecular weight, the average molecular weight being approximately between 5,000 and 10,000. This polymer is also known as "AMODIMETHICONE".

Other silicone cationic polymers which can be used according to the invention correspond to the formula:

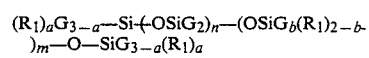

in which

G is chosen from the group consisting of hydrogen, phenyl, OH, $C_1$-$C_8$ alkyl and preferably methyl;

a denotes 0 or an integer from 1 to 3, and preferably equals 0;

b denotes 0 or 1 and preferably equals 1;

the sum $n+m$ is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups:

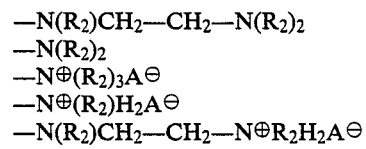

in which $R_2$ is chosen from the group consisting of hydrogen, phenyl, benzyl, a saturated hydrocarbon radical, preferably an alkyl radical containing from 1 to 20 carbon atoms, and $A^\ominus$ denotes a halide ion.

These compounds are described in greater detail in European Patent Application EP No. 95,238. An especially preferred polymer corresponding to this formula is the polymer known as "trimethylsilylAMODIMETHICONE" of formula:

$$(CH_3)_3-Si \left[ -O-\underset{\underset{CH_3}{|}}{\overset{\overset{CH_3}{|}}{Si}}- \right]_n \left[ -O-\underset{\underset{\underset{\underset{NH_2}{|}}{(CH_2)_2}}{\underset{|}{NH}}}{\overset{\overset{CH_3}{|}}{\underset{|}{Si}}}- \right]_m -OSi(CH_3)_3 \quad \text{(II)}$$

Other silicone cationic polymers which can be used according to the invention correspond to the formula:

$$R_4-CH_2-CHOH-CH_2-\overset{\oplus}{N}(R_3)_3Q^{\ominus} \quad \text{(III)}$$

$$(R_3)_3-Si-O\left[-\underset{\underset{R_3}{|}}{\overset{\overset{R_3}{|}}{Si}}-O-\right]_r \left[-\underset{\underset{R_3}{|}}{\overset{\overset{R_3}{|}}{Si}}-O-\right]_s Si-(R_3)_3$$

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably, a $C_1$-$C_{18}$ alkylene radical or a $C_1$-$C_{18}$, and preferably $C_1$-$C_8$, alkyleneoxy radical;

$Q^{\ominus}$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

The cationic surfactants used according to the invention are chosen from the compounds corresponding to the formula:

$$\underset{\underset{R_8}{\diagup} \quad \underset{R_5}{\diagdown}}{\overset{R_7 \diagdown \overset{\oplus}{N} \diagup R_6}{}} \quad X^{\ominus} \quad \text{(IV)}$$

in which:

(1) $R_5$ and $R_6$ denote methyl, $R_7$ and $R_8$ being able, in this case, to have the following meanings:

(i) $R_7$ and $R_8$ denote a linear aliphatic radical, preferably an alkyl radical having from 12 to 22 carbon atoms, an aliphatic radical derived from tallow fatty acids, containing from 14 to 22 carbon atoms, (ii) or alternatively $R_7$ denotes a linear aliphatic radical and preferably an alkyl radical having 14 to 22 carbon atoms, and $R_8$ denotes methyl or benzyl, (iii) or alternatively $R_7$ denotes a ($C_{14}$-$C_{22}$ alkyl)alkylamidopropyl radical and $R_8$ denotes a ($C_{12}$-$C_{16}$ alkyl)alkyl acetate group, (iv) or alternatively $R_7$ denotes a γ-gluconamidopropyl or $C_{16}$-$C_{18}$ alkyl radical and $R_8$ denotes hydroxyethyl, $X^{\ominus}$ denotes an anion such as a halide or methosulphate ion.

(2) $R_5$ denotes an alkylamidoethyl and/or alkenylamidoethyl group in which the alkyl radical containing from 14 to 22 carbon atoms is derived from tallow fatty acids, and $R_6$ and $R_7$ form with the nitrogen atom a 2-alkyl (derived from tallow fatty acids)-4,5-dihydroimidazole heterocyclic system, $R_8$ denotes methyl $X^{\ominus}$ denotes a methosulphate ion.

(3) $R_5$, $R_6$ and $R_7$ form with the nitrogen atom an aromatic heterocyclic system, $R_8$ denotes a $C_{14}$-$C_{18}$ alkyl radical and $X^{\ominus}$ denotes a halide ion.

Among preferred cationic surfactants, the following may be mentioned: dimethylstearylbenzylammonium chloride, trimethyl($C_{20}$-$C_{22}$ alkyl)ammonium chloride also sold under the name "GENAMINE KDM-F" by HOECHST, cetylpyridinium chloride, dimethyl($C_{12}$-$C_{14}$ dialkyl)ammonium chloride, dimethyl-(γ-gluconamidopropyl)hydroxyethylammonium chloride sold under the name "CERAPHYL 60" by VAN DYK, and dimethyldicetylammonium chloride sold under the name "NORANIUM M2 SH".

The cationic polysaccharides preferably used according to the invention have a molecular weight from 10,000 to 3 million, and are chosen from:

(1) cellulose ether derivatives containing quaternary ammonium groups corresponding to the structural formula:

$$\left[ \begin{array}{ccc} R & R & R \\ | & | & | \\ O & O & O \\ \diagdown & | & \diagup \\ & R_{Cell} & \end{array} \right]_y \quad \text{(V)}$$

in which $R_{Cell}$ is the residue of an anhydroglucose unit, y is a number equal to between about 50 and about 20,000 and each R individually denotes a substituent which is a group of general formula:

$$-(C_aH_{2a}-O-)_m(CH_2-\underset{\underset{R_1-\overset{\oplus}{N}-R_9}{\underset{|}{CH_2}}}{\overset{|}{CH}}-O)_{\overline{n}}(C_bH_{2b}-O)_{\overline{p}}(C_cH_{2c})_q-R' \quad \frac{1}{V}[X]^{V-}$$

where a is an integer equal to 2 or 3;

b is an integer equal to 2 or 3;

c is an integer equal to 1 to 3;

m is an integer equal to 0 to 10;

n is an integer equal to 0 to 3;

p is an integer equal to 0 to 10;

q is an integer equal to 0 or 1;

R' is a hydrogen atom or a radical of formula:

$$-\overset{\overset{O}{\|}}{C}-OH, \quad -\overset{\overset{O}{\|}}{C}-O-Na \quad -\overset{\overset{O}{\|}}{C}-O-K, \quad \text{or} \quad -\overset{\overset{O}{\|}}{C}-O-NH_4$$

it being clearly understood that when q equals zero R' denotes —H;

$R_9$, $R_{10}$ and $R_{11}$, taken individually, each represent an alkyl, aryl, aralkyl, alkylaryl, cycloalkyl, alkoxyalkyl or alkoxyaryl radical, each of the radicals $R_9$, $R_{10}$ and $R_{11}$ being able to contain up to 10 carbon atoms, it being clearly understood that when the radical is an alkoxyalkyl radical there are at least two carbon atoms which separate the oxygen atom from the nitrogen atom, and it also being clearly understood that the total number of carbon atoms present in radicals denoted by $R_9$, $R_{10}$ and $R_{11}$ is between 3 and 12;

$R_9$, $R_{10}$ and $R_{11}$, taken together, can denote, with the nitrogen atom to which they are attached, one of the following radicals: pyridine, α-methylpyridine, 3,5-dimethylpyridine, 2,4,6-trimethylpyridine, N-methylpiperidine, N-ethylpiperidine, N-methylmorpholine or N-ethylmorpholine;

X is an anion;

V is an integer equal to the valency of X;

the average value of n per anhydroglucose unit in this cellulose ether is between 0.01 and approximately 1, and the average value (m+n+p+q) per anhydroglucose unit in this cellulose ether is between approximately 0.01 and approximately 4.

The most especially preferred polymers are those corresponding to the formula (V) above in which a and b are equal to 2, q is equal to 0, m, n and p having the values mentioned above, R' denotes hydrogen and $R_9$, $R_{10}$ and $R_{11}$ denote methyl. The average values per anhydroglucose unit are from 0.35 to 0.45 for n and 1 to 2 for the sum m+p, X denotes chloride.

The preferred ethers according to the invention have viscosities at 25° C. from 50 to 35,000 centipoises in aqueous solution at 2% strength by weight, measured by ASTM method D-2364-65 (Brookfield model LVF viscometer, 30 rpm, spindle no. 2), and those especially preferred are those sold by Union Carbide Corporation under the tradenames "JR-125", "JR-400" and "JR-30M", which denote, respectively, a polymer of the type described above of viscosity equal to 125 centipoises, 400 centipoises and 30,000 centipoises; and LR such as LR 400 and LR 30M.

(2) A cationic cellulose derivative prepared according to the process described in U.S. Pat. No. 4,131,576, which is a copolymer of cellulose or of a cellulose derivative grafted with a water-soluble quarternary ammonium monomer.

The water-soluble quaternary ammonium monomers are chosen, in particular, from (methacryloylethyl)trimethylammonium, (methacrylamidopropyl)trimethylammonium and dimethyldiallylammonium salts, and in particular the halides such as chlorides or the methosulphates.

The cellulose derivatives are preferably chosen from hydroxyalkylcelluloses such as hydroxymethyl- or hydroxyethyl- or hydroxypropylcelluloses.

The especially preferred products are those sold under the name "CELQUAT L 200" and "CELQUAT H100" by National Starch.

The cyclopolymers used according to the invention have a molecular weight from 20,000 to 3,000,000, containing units corresponding to the formulae (X) or (X') below:

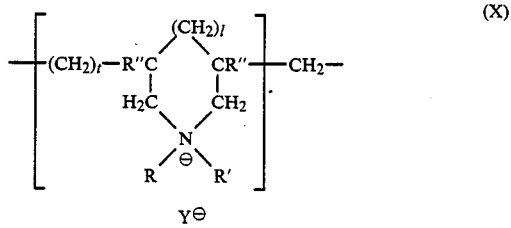

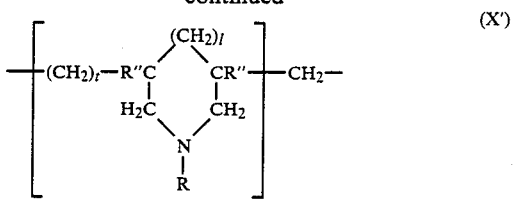

in which l and t are equal to 0 or 1 and l+t equals 1, R" denotes hydrogen or methyl, R and R' denote, independently of each other, an alkyl group having from 1 to 22 carbon atoms, a hydroxyalkyl group in which the alkyl group preferably has 1 to 5 carbon atoms, or a lower amidoalkyl group, and in which R and R' can form, conjointly with the nitrogen atom to which they are attached, heterocyclic groups such as piperidinyl or morpholinyl, as well as copolymers containing, in addition to the units of formula (X) or (X'), units derived from acrylamide or diacetone acrylamide, and $Y^\ominus$ denotes an anion such as bromide, chloride, acetate, borate, citrate, tartrate, bisulphate, bisulphite, sulphate or phosphate.

Among the cyclopolymers defined above, those most especially preferred are the homopolymer of dimethyldiallylammonium chloride sold by MERCK under the name "MERQUAT 100" having a molecular weight below 100,000, and the dimethyldiallylammonium chloride/acrylamide copolymer having a molecular weight above 500,000 and sold under the name "MERQUAT 550" by MERCK.

These polymers are described, in particular, in French Pat. No. 2,080,759 and its certificate of addition 2,190,406.

The especially preferred cationic polymers are cationic cellulose derivatives, the products sold under the name "CELQUAT L 200" and "CELQUAT H 100" and the known cyclopolymers, the products sold under the name "HERAUAT 550".

The soaps used in the compositions according to the invention are preferably present in proportions of between approximately 1 and 8% by weight relative to the total weight of the composition.

The silicone cationic polymers defined above are used in proportions of between approximately 0.05 and 2.5% by weight.

The cationic surfactants are preferably used in proportions of between approximately 0.1 and 2% by weight relative to the total weight of the composition.

The cationic polymers are preferably used in proportions of between approximately 0.05 and 5% by weight relative to the total weight of the composition.

The compositions according to the invention can also contain, according to a preferred embodiment, nonionic surfactants, and in particular polyoxyethylenated or polyglycerolated fatty alcohols or alkylphenols.

The especially preferred cationic silicone polymers can be introduced in the compositions according to the invention in the form of emulsions containing the silicone polymer together with the nonionic and cationic surfactants mentioned above.

One emulsion of this type which is especially preferred and used according to the invention consists of the composition sold under the tradename "DOW CORNING 929" (DC 929) cationic emulsion by DOW CHEMICAL COMPANY, which is a combination of:

(a) "AMODIMETHICONE" defined above (b) trimethyl(tallow alkyl)ammonium chloride corresponding to the formula:

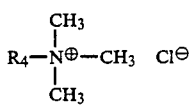

where $R_4$ denotes a mixture of alkenyl and/or alkyl radicals having 14 to 22 carbon atoms and derived from tallow fatty acids, and (c) polyoxyethylenated nonylphenol corresponding to the formula:

$$C_9H_{19}-C_6H_4-(OC_2H_4)_{10}-OH.$$

Another emulsion based on silicone cationic polymers according to the present invention is the composition sold under the name "DOW CORNING Q2 7224" by DOW CORNING, which is a combination of:

(a) trimethylsilylAMODIMETHICONE defined above (b) polyoxyethylenated octylphenol of formula:

$$C_8H_{17}-C_6H_4-(OCH_2CH_2)_nOH$$

where $n=40$ (c) polyoxyethylenated lauric alcohol of formula:

$$C_{12}H_{25}-(OCH_2-CH_2)_nOH$$

where $n=6$ (d) glycol.

According to a preferred embodiment, the compositions according to the invention can contain, in addition, a fatty amine oxide corresponding to the formula:

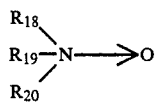

in which $R_{18}$ denotes an alkyl, alkenyl, $C_{10}-C_{16}$ hydroxyalkyl or ($C_{12}-C_{18}$ alkyl)amidopropyl group, and $R_{19}$ and $R_{20}$, which may be identical or different, denote a methyl, ethyl, propyl, hydroxyethyl or hydroxypropyl group.

An especially preferred compound belonging to this family is dodecyldimethylamine oxide (AMMONYX LO) or the (alkylamidopropyl)dimethylamine oxide in which the alkyl radical is derived from coconut fatty acids and which is sold under the name "AMINOXYD WS 25". These amine oxides are preferably present in proportions of between 0 and 10% by weight.

The compositions according to the invention preferably take the form of a liquid thickened to a greater or lesser extent, gel form or cream form, or are packaged as an aerosol. They can contain, in addition to the combination defined above, different adjuvants customarily used in cosmetics such as perfumes, preservatives, sequestering agents, thickeners, emulsifiers, emollients, foam stabilisers, and acidifying or alkalinising agents.

The thickeners are chosen, in particular, from sodium alginate, gum arabic, cellulose derivatives such as methylcellulose, hydroxymethylcellulose, hydroxyethylcellulose, hydroxypropylcellulose, and guar gum or its derivatives. Thickening of the compositions can also be achieved by mixing polyethylene glycol and polyethylene glycol stearate or distearate, or by a mixture of phosphoric ester and amides.

These compositions can also contain, in addition, other cosmetically acceptable solvents such as monoalcohols, polyalcohols, glycol ethers, and fatty acid esters, used alone or mixed. Among solvents, there may be mentioned, more especially, lower alcohols such as ethanol, n-propanol, isopropanol, n-butanol, polyalcohols such as ethylene glycol, diethylene glycol, propylene glycol, and glycol ethers such as mono- or diethylene glycol alkyl ethers.

The compositions according to the invention can be used as shampoos, and are in this case applied on soiled, wet hair. After the hair is massaged, it is frinsed and the shampoo is generally applied once again, followed by rinsing again with water.

These compositions can also be used as emollient shampoos, applied immediately after dyeing. The compositions according to the invention can finally be used as a vehicle for colouring products. In this case, the composition contains in addition direct dyes chosen from nitrated derivatives of the benzene series, azo, anthraquinone or naphthoquinone dyes, indoamines, indoanilines or indophenols.

These dyeing compositions can contain, in addition, a solvent other than water in proportions of 0.5 to 10% by weight, chosen from lower alcohols, glycols and glycol ethers.

The dyes in this embodiment are used in proportions varying between 0.01 and 3% by weight, and preferably between 0.05 and 1.5% by weight, relative to the total weight of the composition.

These dyeing compositions are applied on soiled hair or on hair which has previously been washed, and after an exposure time, generally between 2 and 30 minutes and preferably 5 to 10 minutes, the hair is rinsed.

The examples which follow are intended to illustrate the present invention without in any way being limitative in nature.

EXAMPLE 1

The following composition is prepared:

| | |
|---|---|
| lauric acid | 3 g |
| 2-amino-2-methyl-1-propanol | 1.34 g |
| coconut ethanolamide | 1 g |
| dimethylbenzylstearylammonium chloride in 94% strength solution, sold under the name "AMMONYX 4002" by ONYX | 1 g |
| cationic emulsion DC 929, sold by DOW CHEMICAL COMPANY | 1.5 g |
| CELQUAT L 200 | 0.5 g |
| (cocamidopropyl)dimethylamine oxide in 35% strength solution, sold under the name "AMINOXID WS35" by GOLDSCHMIDT | 8 g |
| diethylenetriaminepentaacetic acid pentasodium salt | 2 g |
| hydroxypropylated guar gum, sold under the name "JAGUAR HP60" by MEYHALL | 0.6 g |
| tartaric acid qs | pH 7.5 |
| perfume, preservative qs | |
| water qs | 100 |

This composition is used as a shampoo. It is applied on soiled, wet hair. After the hair is washed and massaged for a few minutes, a second application is made and the hair is rinsed. The hair is then very easy to disentangle. The dried hair is supple, shiny, soft and easy to style.

The examples which follow in the Tables are intended to illustrate other compositions according to the invention.

TABLE I

|  | Example No. | | | |
| --- | --- | --- | --- | --- |
|  | 2 | 3 | 4 | 5 |
| lauric acid | 3 g | 3 g | 3 g | — |
| oleic acid | — | — | — | 4.5 |
| triethanolamine | 4.94 | 2.5 | 4.94 | 2.5 |
| coconut ethanolamide | 1 | 2 | 1 | — |
| dimethylbenzylstearylammonium chloride, in 94% strength solution (AMMONYX 4002 from ONYX) | — | 1 | — | 1 |
| trimethyl($C_{20}$–$C_{22}$ alkyl)-ammonium chloride in 80% strength solution (GENAMINE KDM.F from HOECHST) | 1 | — | — | — |
| dimethyl($C_{12}$–$C_{14}$ dialkyl)-ammonium chloride in 75% strength solution (NORAMIUM M2C from CECA) | — | — | 1 | — |
| cationic emulsion DC 929 | 1.71 | 1.5 | 1.71 | 1 |
| CELQUAT L 200 | 0.4 | 0.3 | 0.4 | 0.4 |
| (coconut alkyl)amidopropyldimethylamine oxide in 35% strength solution (AMINOXID WS 35 from GOLDSCHMIDT) | 8.55 | 7.5 | 8.55 | 5 |
| diethylenetriaminepentaacetic acid pentasodium salt | 2 | 2 | 2 | 2 |
| hydroxypropylated guar gum (JAGUAR HP60 from MEYHALL) | 0.4 | 0.2 | 0.4 | — |
| tartaric acid qs pH | 7.5 | 8 | 8 | 7.5 |
| perfume, preservative | qs | qs | qs | qs |
| water qs | 100 | 100 | 100 | 100 |

EXAMPLE 6

The following dyeing composition is prepared:

| | |
| --- | --- |
| lauric acid | 2 g |
| 2-amino-2-methyl-1-propanol | 0.89 g |
| coconut ethanolamide | 2 g |
| AMMONYX 4002 (94% strength solution) | 1 g |
| cationic emulsion DC 929 | 1.71 g |
| CELQUAT L 200 | 0.4 g |
| hydroxypropylated guar gum JAGUAR HP 60 | 0.2 g |
| 2-($\beta$-hydroxyethyl)amino-5-($\beta,\gamma$-dihydroxypropyloxy)-1-nitrobenzene | 0.09 g |
| 3-methylamino-4-nitrophenyl $\beta,\gamma$-dihydroxypropyl ether | 0.04 g |
| tartaric acid qs | pH 8 |
| perfume, preservative qs | |
| water qs | 100 g |

This composition is used as a "colouring balm". Applied on light chestnut-coloured hair, after 15 minutes' exposure, rinsing and drying, shiny, soft hair is obtained, the shade of which possesses golden glints, and which is easy to style and disentangle.

Table II below gives other examples of embodiment of compositions according to the invention also used as a "colouring balm".

TABLE II

|  | Example No. | | | | |
| --- | --- | --- | --- | --- | --- |
|  | 7 | 8 | 9 | 10 | 11 |
| lauric acid | 2 | 2 | 2 | 3 | 2 |
| 2-amino-2-methyl-1-propanol | 0.89 | 0.89 | 0.89 | 1.34 | 0.89 |
| coconut ethanolamide | 2 | 2 | 2 | 2 | 2 |
| AMMONYX 4002 (94% strength solution) | 1 | — | — | 1 | 1 |
| GENAMINE KDM-F (80% strength solution) | — | 1 | — | — | — |
| cetylpyridinium chloride | — | — | 1 | — | — |
| cationic emulsion DC 929 | 1.71 | 1.71 | 2.2 | 1.71 | 1.71 |
| CELQUAT L 200 | 0.4 | 0.4 | 0.7 | 0.4 | 0.4 |
| hydroxypropylated guar gum JAGUAR HP60 | 0.2 | 0.2 | 0.1 | 0.7 | 0.2 |
| 3-methylamino-4-nitrophenyl $\beta,\gamma$-dihydroxypropyl ether | — | 0.06 | 0.2 | — | — |
| 3-nitro-2-aminophenol | 0.05 | — | — | 0.05 | — |
| 3-nitro-4-aminophenol | 0.025 | — | — | 0.025 | — |
| 4-($\beta$-hydroxyethyl)amino-3-nitrophenol | 0.01 | — | 0.2 | 0.01 | 0.2 |
| 1-methylamino-2-nitro-4-[methyl($\beta$-hydroxyethyl)amino]benzene | — | 0.1 | — | — | 0.1 |
| tartaric acid qs pH | 8 | 8 | 8 | 8 | 8 |
| perfume, preservative qs | — | — | — | — | — |
| water qs | 100 | 100 | 100 | 100 | 100 |
| shade (glints) | golden | beige | coppery | golden | dark auburn |

EXAMPLE 12

The following composition is prepared:

| | |
| --- | --- |
| lauric acid | 3 g |
| sodium hydroxide | 0.64 g |
| coconut ethanolamide | 1 g |
| dimethylbenzylstearylammonium chloride (AMMONYX 4002 from ONYX) in 94% strength solution | 1 g |
| cationic emulsion DC 929 | 1.71 g |
| CELQUAT L 200 | 0.4 g |
| diethylenetriaminepentaacetic acid pentasodium salt | 2 g |
| tartaric acid qs | pH 7.8 |
| preservative qs | |
| water qs | 100 g |

This composition is used as a shampoo.

EXAMPLE 13

The following composition is prepared:

| | |
| --- | --- |
| lauric acid | 3 g |
| triethanolamine | 4.94 g |
| coconut ethanolamide | 1 g |
| cocamidopropyldimethylamine oxide ("AMINOXID WS 35" from Goldschmidt) in 35% strength aqueous solution | 8.55 g |
| dimethylbenzylstearylammonium chloride (AMMONYX 4002 from Onyx) in 94% strength solution | 1 g |
| ucar silicone ALE 56 in 35% strength solution | 1.71 g |
| CELQUAT L 200 | 0.4 g |
| diethylenetriaminepentaacetic acid pentasodium salt | 2 g |
| perfume, preservative qs | |
| tartaric acid qs | pH 7.8 |
| water qs | 100 g |

This composition is used as a shampoo.

EXAMPLE 14

The following composition is prepared:

| | |
| --- | --- |
| lauric acid | 3 g |
| triethanolamine | 2.5 g |
| coconut ethanolamide | 1 g |
| trimethylbenzylstearylammonium chloride (AMMONIX 4002 from Onyx) in 94% strength solution | 1 g |

| | |
|---|---|
| cationic emulsion DC 929 | 1.71 g |
| dimethyldiallylammonium chloride/acrylamide copolymer of molecular weight greater than 500,000 (MERQUAT 550 from Merck) in 8% strength solution | 1.25 g |
| diethylenetriaminepentaacetic acid pentasodium salt | 2 g |
| tartaric acid qs | pH 7.8 |
| perfume, preservative qs | |
| water qs | 100 g |

This composition is used as a shampoo.

EXAMPLE 15

The following composition is prepared:

| | |
|---|---|
| lauric acid | 3 g |
| triethanolamine | 4.94 g |
| coconut ethanolamide | 1 g |
| cocamidopropyldimethylamine oxide sold under the name "AMINOXID WS 35" by GOLDSCHMIDT in 35% strength solution | 8.55 g |
| trimethyl($C_{20}$–$C_{22}$ alkyl)ammonium chloride (GENAMINE KDM-F from Hoechst) in 80% strength solution | 1 g |
| cationic emulsion DC 929 | 1.71 g |
| CELQUAT L 200 | 0.4 g |
| hydroxypropylated guar gum (JAGUAR HP from MEYHALL) | 0.4 g |
| tartaric acid qs | pH 7.5 |
| diethylenetriaminepentaacetic acid pentasodium salt | 2 g |
| perfume, preservative qs | |
| water qs | 100 g |

This composition is used as a shampoo.

EXAMPLE 16

The following composition is prepared:

| | |
|---|---|
| lauric acid | 6 g |
| triethanolamine | 5 g |
| coconut ethanolamide | 1 g |
| dimethyldicetylammonium chloride ("NORANIUM M2 SH" from Ceca) in 75% strength solution | 1 g |
| cationic emulsion DC 929 | 1.71 g |
| CELQUAT L 200 | 0.4 g |
| cocamidopropyldimethylamine oxide ("AMINOXID WS 35" from GOLDSCHMIDT) in 35% strength solution | 8.55 g |
| diethylenetriaminepentaacetic acid pentasodium salt | 2 g |
| perfume, preservative qs | |
| tartaric acid qs | pH 7.8 |
| water qs | 100 g |

This composition is used as a shampoo.

EXAMPLE 17

The following composition is prepared:

| | |
|---|---|
| lauric acid | 3 g |
| triethanolamine | 2.5 g |
| cationic emulsion DC 929 | 1.71 g |
| dimethyl-(γ-gluconamidopropyl)hydroxyethylammonium chloride ("CERAPHYL 60" from Van Dyk) in 60% strength solution | 1 g |
| "JR 400" from Union Carbide Corporation | 0.1 g |
| diethylenetriaminepentaacetic acid pentasodium salt | 2 g |
| tartaric acid qs | pH 7.8 |
| perfume, preservative qs | |
| water qs | 100 g |

This composition is used as a shampoo.

EXAMPLE 18

The following composition is prepared:

| | |
|---|---|
| lauric acid | 3 g |
| triethanolamine | 4.94 g |
| ucar silicone ALE 56 in 35% strength solution | 1.71 g |
| ($C_{16}$ alkyl)dimethylhydroxyethylammonium chloride in 30% strength solution | 1 g |
| dimethyldiallylammonium chloride homopolymer having a molecular weight below 100,000 ("MERQUAT 100" from Merck) in 40% strength solution | 6.25 g |
| diethylenetriaminepentaacetic acid pentasodium salt | 2 g |
| tartaric acid qs | pH 8 |
| perfume, preservative qs | |
| water qs | 100 g |

This composition is used as a shampoo.

EXAMPLE 19

The following composition is prepared:

| | |
|---|---|
| lauric acid | 3 g |
| triethanolamine | 4.94 g |
| coconut ethanolamide | 1 g |
| dimethylbenzylstearylammonium chloride (AMMONIX 4002 from Onyx) in 94% strength solution | 1 g |
| CELQUAT L 200 | 0.4 g |
| cationic emulsion sold under the name "DOW CORNING Q2 7224" by DOW | 1.71 g |
| cocamidopropyldimethylamine oxide ("AMINOXID WS 35" from Goldschmidt) in 35% strength solution | 8.55 g |
| diethylenetriaminepentaacetic acid pentasodium salt | 2 g |
| tartaric acid qs | pH 7.8 |
| perfume, preservative qs | |
| water qs | 100 |

This composition is used as a shampoo.

EXAMPLE 20

The following composition is prepared:

| | |
|---|---|
| lauric acid | 3 g |
| triethanolamine | 2.5 g |
| JR 400 from "Union Carbide" | 0.05 g |
| cationic emulsion DC 929 | 1.71 g |
| distearyldimethylammonium chloride | 1 g |
| diethylenetriaminepentaacetic acid pentasodium salt | 2 g |
| tartaric acid qs | pH 8 |
| perfume, preservative qs | |
| water qs | 100 g |

This composition is used as a shampoo.

Similar results are observed for the compositions of Examples 12 to 20 as with that of Example 1.

We claim:

1. Detergent cosmetic composition containing a direct dye, which composition is stable on storage, comprising in a cosmetically acceptable aqueous medium:

(a) an alkali metal or alkanolamine fatty acid soap present in proportions of between approximately 1 and 8% by weight,
(b) a silicone cationic polymer present in proportions of between 0.05 and 2.5% by weight consisting of a polysiloxane having one of the following meanings:
(i) polymers of formula:

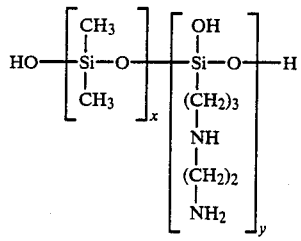
(I)

in which x and y are integers which depend on the molecular weight, which is approximately between 5,000 and 10,000,
(ii) polymers of formula:

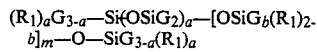
(II)

in which
G is chosen from the group consisting of hydrogen, phenyl, OH and $C_1$–$C_8$ alkyl, a denotes 0 or an integer from 1 to 3 and b denotes 0 or 1, the sum n+m signifies an integer from 1 to 2,000, n denoting a number from 0 to 1,999 and m denoting a number from 1 to 2,000, $R_1$ is a monovalent radical of formula $C_qH_{2q}L$ in which q is an integer from 2 to 8 and L is chosen from the groups:

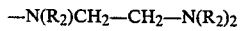

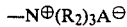

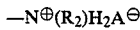

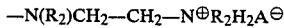

in which $R_2$ denotes hydrogen or phenyl or benzyl groups, or a saturated hydrocarbon radical, and $A^\ominus$ denotes a halide ion, or:
(iii) polymers of formula:

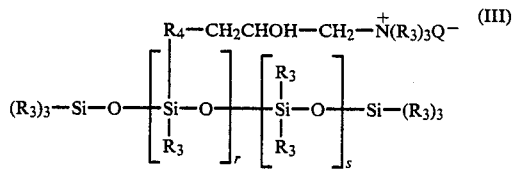
(III)

in which $R_3$ denotes a monovalent hydrocarbon radical having from 1 to 18 carbon atoms, $R_4$ denotes a divalent hydrocarbon radical, $Q^\ominus$ is a halide ion, r denotes an average statistical value from 2 to 20 and s denotes an average statistical value from 20 to 200,
(c) a cationic surfactant used in proportions of between approximately 0.05 and 2.5% by weight and (d) a cationic polymer present in proportions of between 0.05 and 5% by weight chosen from
(i) a quaternary derivative of cellulose ethers corresponding to the formula:

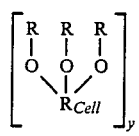
(IV)

where $R_{Cell}$ is the residue of an anhydroglucose unit, y is a number equal to between about 50 and about 20,000 and each R individually denotes a substitutent which is a group of general formula:

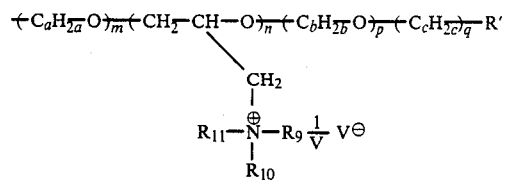

where
a is an integer equal to 2 or 3;
b is an integer equal to 2 or 3;
c is an integer equal to 1 to 3;
m is an integer equal to 0 to 10;
n is an integer equal to 0 to 3;
p is an integer equal to 0 to 10;
q is an integer equal to 0 or 1;
R' is a hydrogen atom or a radical of formula:

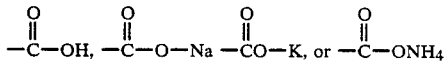

with the proviso that when p equals zero R' denotes —H;
$R_9$, $R_{10}$ and $R_{11}$, taken individually, each represent an alkyl, aryl, aralkyl, alkylaryl, cycloalkyl, alkoxyalkyl or alkoxyaryl radical, each of the radicals $R_9$, $R_{10}$ and $R_{11}$ being able to contain up to 10 carbon atoms, it being clearly understood that when the radical is an alkoxyalkyl radical there are at least two carbon atoms which separate the oxygen atom from the nitrogen atom, and it also being clearly understood that the total number of carbon atoms present in radicals denoted by $R_9$, $R_{10}$ and $R_{11}$ is between 3 and 12;
$R_9$, $R_{10}$ and $R_{11}$, taken together, can denote, with the nitrogen atom to which they are attached, one of the following radicals; pyridine, α-methylpyridine, 3,5-dimethylpyridine, 2,4,6-trimethylpyridine, N-methylpiperidine, N-ethylpiperidine, N-methylmorpholine or N-ethylmorpholine; X is an anion;
V is an integer equal to the valency of X;
the average value of n per anhydroglucose unit in this cellulose ether is between 0.01 and approximately 1, and the average value of (m+n+p+q) per anhydroglucose unit in this cellulose ether is between approximately 0.01 and approximately 4, (ii) a copolymer of cellulose or cellulose derivative grafted with a water-soluble quaternary ammonium monomer is a graft copolymer of hydroxyalkylcellulose with a (methacryloylethyl)trimethylammonium salt, a (methacrylamidopropyl)-trimethylammonium salt or a dimethyldiallylammonium salt, (iii) a cationic cyclopolymer having a molecular weight of between 20,000 and 3,000,000 and containing units of formulae:

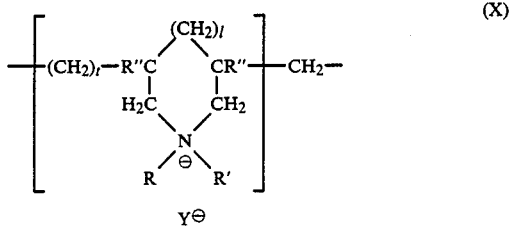

(X)

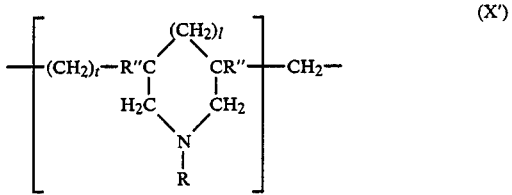

(X')

in which l and t are equal to 0 or 1 and l+t=1, R" denotes hydrogen or methyl, R and R' denote independently of each other an alkyl group having from 1 to 22 carbon atoms, a hydroxyalkyl group in which the alkyl group preferably has 1 to 5 carbon atoms, or a lower amidoalkyl group, and in which R and R' can also denote, conjointly with the nitrogen atom to which they are attached, heterocyclic groups chosen from piperidinyl or morpholinyl groups, as well as copolymers containing units of formula (X) or (X') and acrylamide and diacetone acrylamide units, $Y^\ominus$ being an anion chosen from bromide, chloride, acetate, borate, citrate, tartrate, bisulphate, bisulphite, sulphate and phosphate, (e) direct dyes selected from the group consisting of nitrobenzene derivatives, azo, anthraquinone and naphthoquinone dyes, indoamines, indoanilines and indophenols, present in proportions of between approximately 0.01 and 3% by weight.

2. Composition according to claim 1, wherein the soaps are selected from the group consisting of alkali metal salts and alkanolamine salts of $C_{12}$-$C_{18}$ fatty acids in which the fatty chain is saturated or unsaturated.

3. Composition according to claim 2, wherein the soaps are salts of lauric, palmitic or oleic acid.

4. Composition according to claim 1, wherein the cationic surfactants are compounds of formula:

(V)

in which:
(1) when $R_5$ and $R_6$ denote methyl, $R_7$ and $R_8$ have the following meanings:
 (i) $R_7$ and $R_8$ denote a linear aliphatic radical,
 (ii) $R_7$ denotes a linear aliphatic radical and $R_8$ denotes methyl or benzyl,
 (iii) $R_7$ denotes an alkylamidopropyl radical and $R_8$ denotes an alkyl acetate group,
 (iv) $R_7$ denotes a γ-gluconamidopropyl or $C_{16}$-$C_{18}$ alkyl radical and $R_8$ denotes a hydroxyethyl,
 $X^\ominus$ denotes a halide or $CH_3SO_4^\ominus$ anion;
(2) $R_5$ denotes an alkylamidoethyl and/or alkenylamidoethyl group in which the alkyl radical having from 14 to 22 carbon atoms is derived from tallow fatty acids, and $R_6$ and $R_7$ form with the nitrogen a 2-alkyl-4,5-dihydroimidazole heterocyclic system,
$R_8$ denotes methyl, and
$X^\ominus$ denotes a methosulphate anion;
(3) $R_5$, $R_6$ and $R_7$ form with the nitrogen atom an aromatic heterocyclic system, $R_8$ denotes a $C_{14}$-$C_{18}$ alkyl radical and $X^\ominus$ denotes a halide anion.

5. Composition according to claim 1, wherein the cationic surfactant is selected from the group comprising dimethylstearylbenzylammonium chloride, trimethyl-($C_{20}$-$C_{22}$ alkyl)ammonium chloride, cetylpyridinium chloride, dimethyl($C_{12}$-$C_{14}$ dialkyl)ammonium chloride, dimethyl(γ-gluconamidopropyl)hydroxyethylammonium chloride and dimethyldicetylammonium chloride.

6. Composition according to claim 1, containing in addition a nonionic surfactant.

7. Composition according to claim 6, wherein the nonionic surfactant is a polyoxyethylenated or polyglycerolated alcohol or alkylphenol.

8. Composition according to claim 1, containing in addition a fatty amine oxide of formula:

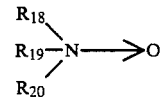

in which $R_{18}$ denotes an alkyl, alkenyl, $C_{10}$-$C_{16}$ hydroxyalkyl or ($C_{12}$-$C_{18}$ alkyl)amidopropyl group, and $R_{19}$ and $R_{20}$, which may be identical or different, denote a methyl, ethyl, propyl, hydroxyethyl or hydroxypropyl group.

9. Composition according to claim 1, in which the silicone cationic polymer is present in the form of an emulsion comprising (a) a polymer corresponding to the formula:

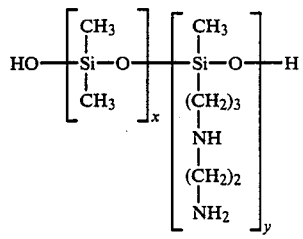

in which x and y are integers which depend on the molecular weight, which is approximately between 5,000 and 10,000, (b) a compound corresponding to the formula:

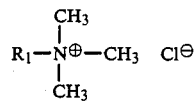

where $R^1$ denotes a mixture of alkenyl and/or alkyl radicals having 14 to 22 carbon atoms and derived from tallow fatty acids, and
(c) a compound of the formula:

$$C_9H_{19}-C_6H_4-(OC_2H_4)_{10}-OH.$$

10. Composition according to claim 1, in which the silicone cationic polymer has the formula:

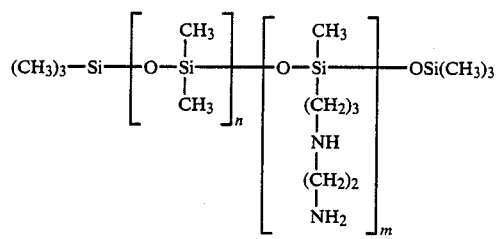

and which further comprises
a compound of formula:

$$C_8H_{17}-C_6H_4-(OCH_2CH_2)_nOH$$

wherein n=40,
a compound of the formula:

$$C_{12}H_{25}-(OCH_2-CH_2)_nOH$$

where n=6 and glycol.

11. Composition according to claim 1, which is under the form of a liquid thickened, gel form or cream form, or is packaged as an aerosol.

12. Composition according to claim 1, containing in addition one or more cosmetically acceptable adjuvants chosen from perfumes, preservatives, sequestering agents, thickeners, emulsifiers, emollients, foam stabilisers, and acidifying and alkalizing agents.

13. Process for washing the hair, comprising the application on hair of a composition as defined in claim 1, followed by the rinsing of hair.

14. Process for colouring the hair, wherein the composition as defined in claim 1 is applied on the damp hair, and, after an exposure time sufficient to impregnate and colour the hair, the latter is rinsed with water.

15. Detergent cosmetic composition containing a direct dye, which composition is stable on storage, comprising in a cosmetically acceptable aqueous medium:
(a) an alkali metal or alkanolamine fatty acid soap present in proportions of between approximately 1 and 8% by weight,
(b) a silicone cationic polymer present in proportions of between 0.05 and 2.5% by weight consisting of a polysiloxane having one of the following meanings:
(i)

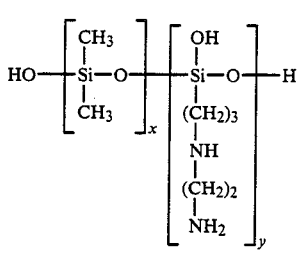

in which x and y are integers which depend on the molecular weight, which is approximately between 5,000 and 10,000,
(ii) polymers of formula:

$$(R_1)_aG_{3\text{-}a}-Si(OSiG_2)_n-[OSiG_b(R_1)_{2\text{-}b}]_m-O-SiG_{3\text{-}a}(R_1)_a \quad (II)$$

in which
G is chosen from the group consisting of hydrogen, phenyl, OH and $C_1$-$C_8$ alkyl, a denotes 0 or an integer from 1 to 3 and b denotes 0 or 1,
the sum n+m signifies an integer from 1 to 2,000, n denoting a number from 0 to 1,999 and m denoting a number from 1 to 2,000, $R_1$ is a monovalent radical of formula $C_qH_{2q}L$ in which q is an integer from 2 to 8 and L is chosen from the groups:
—$N(R_2)CH_2$—$CH_2$—$N(R_2)_2$
—$N(R_2)_2$
—$N^{\oplus}(R_2)_3A^{\ominus}$
—$N^{\oplus}(R_2)H_2A^{\ominus}$
—$N(R_2)CH_2$—$CH_2$—$N^{\oplus}R_2H_2A^{\ominus}$
in which $R_2$ denotes hydrogen or phenyl or benzyl groups, or a saturated hydrocarbon radical, and $A^{\ominus}$ denotes a halide ion, or:
(iii) polymers of formula:

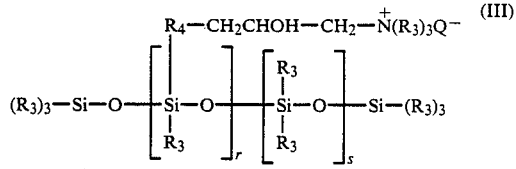

in which $R_3$ denotes a monovalent hydrocarbon radical having from 1 to 18 carbon atoms, $R_4$ denotes a divalent hydrocarbon radical, $Q^{\ominus}$ is a halide ion, r denotes an average statistical value from 2 to 20 and s denotes an average statistical value from 20 to 200,
(c) a cationic surfactant used in proportions of between approximately 0,05 and 2,5% by weight and
(d) a cationic polymer present in proportions of between 0.05 and 5% by weight chosen from:
(i) a quaternary derivative of cellulose ethers corresponding to the formula:

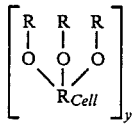

where $R_{Cell}$ is the residue of an anhydroglucose unit, y is a number equal to between about 50 and about 20,000 and each R individually denotes a substituent which is a group of general formula:

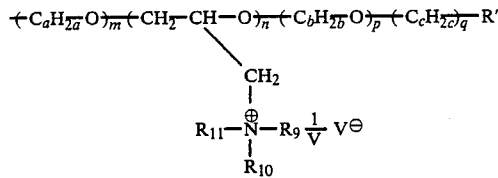

where
a is an integer equal to 2 or 3;
b is an integer equal to 2 or 3;
c is an integer equal to 1 to 3;
m is an integer equal to 0 to 10;
n is an integer equal to 0 to 3;
p is an integer equal to 0 to 10;
q is an integer equal to 0 or 1;
R' is a hydrogen atom or a radical of formula:

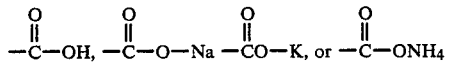

with the proviso that when p equals zero R' denotes —H;
$R_9$, $R_{10}$ and $R_{11}$, taken individually, each represent an alkyl, aryl, aralkyl, alkylaryl, cycloalkyl, alkoxyalkyl or alkoxyaryl radical, each of the radicals $R_9$, $R_{10}$ and $R_{11}$ being able to contain up to 10 carbon atoms, with the proviso that when the radical is an alkoxyalkyl radical there are at least two carbon atoms which separate the oxygen atom from the nitrogen atom, the total number of carbon atoms present in radicals denoted by $R_9$, $R_{10}$ and $R_{11}$ being between 3 and 12;
$R_9$, $R_{10}$ and $R_{11}$, taken together, can denote, with the nitrogen atom to which they are attached, one of the following radicals: pyridine, α-methylpyridine, 3,5-dimethylpyridine, 2,4,6-trimethylpyridine, N-methylpiperidine, N-ethylpiperidine, N-methylmorpholine or N-ethylmorpholine; X is an anion;
V is an integer equal to the valency of X;
the average value of n per anhydroglucose unit in this cellulose ether is between 0.01 and approximately 1, and the average value of (m+n+p+q) per anhydroglucose unit in this cellulose ether is between approximately 0.01 and approximately 4, (ii) a copolymer of cellulose or cellulose derivative grafted with a water-soluble quaternary ammonium monomer is a graft copolymer of hydroxyalkylcellulose with a (methacryloylethyl)trimethylammonium salt, a (methacrylamidopropyl)-trimethylammonium salt or a dimethyldiallylammonium salt,
(iii) a cationic cyclopolymer having a molecular weight of between 20,000 and 3,000,000 and containing units of formulae:

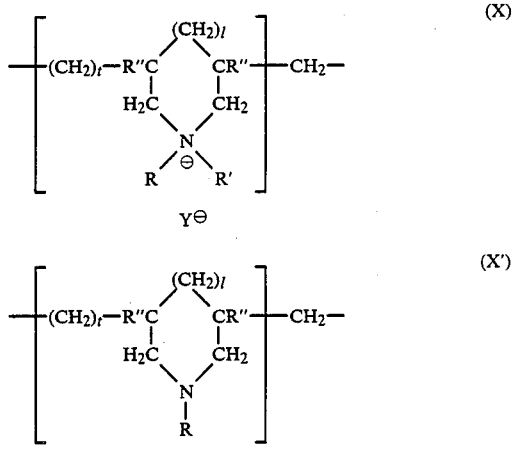

in which l and t are equal to 0 or 1 and l+t=1, R" denotes hydrogen or methyl, R and R' denote independently of each other an alkyl group having from 1 to 22 carbon atoms, a hydroxyalkyl group in which the alkyl group has 1 to 5 carbon atoms, or a lower amidoalkyl group, and in which R and R' can also denote, conjointly with the nitrogen atom to which they are attached, heterocyclic groups chosen from piperidinyl or morpholinyl groups, as well as copolymers containing of formula (X) or (X') and acrylamide and diacetone acrylamide units, $Y^\ominus$ being an anion chosen from bromide, chloride, acetate, borate, citrate, tartrate, bisulphate, bisulphite, sulphate and phosphate, and containing, in addition, direct dyes selected from the group consisting of nitrobenzene derivatives, azo, anthraquinone and naphthoquinone dyes, indoamines, indoanilines and indophenols, present in proportions of between approximately 0.01 and 3% by weight.

16. Process for colouring the hair, wherein the composition as defined in claim 15 is applied on the damp hair, and, after an exposure time sufficient to impregnate and colour the hair, the latter is rinsed with water.

* * * * *